United States Patent
Melkent et al.

(10) Patent No.: US 7,658,766 B2
(45) Date of Patent: Feb. 9, 2010

(54) INTERVERTEBRAL IMPLANTS WITH COVERED INNER CHAMBER AND METHODS OF USE

(75) Inventors: Anthony J. Melkent, Memphis, TN (US); Joseph Patrick Pizzurro, Jr., Collierville, TN (US); John White, Bartlett, TN (US)

(73) Assignee: Warsaw Orthopedic, Inc.

( * ) Notice: Subject to any disclaimer, the term of this patent is extended or adjusted under 35 U.S.C. 154(b) by 126 days.

(21) Appl. No.: 11/415,325

(22) Filed: May 1, 2006

(65) Prior Publication Data
US 2007/0255416 A1 Nov. 1, 2007

(51) Int. Cl.
A61F 2/44 (2006.01)
(52) U.S. Cl. .................... 623/17.11; 623/17.16
(58) Field of Classification Search ............ 606/61, 606/246, 279; 623/17.11–17.16
See application file for complete search history.

(56) References Cited

U.S. PATENT DOCUMENTS

| | | | |
|---|---|---|---|
| 4,501,269 A | | 2/1985 | Bagby |
| 4,641,370 A | * | 2/1987 | Oyamada .................... 455/348 |
| 5,306,309 A | | 4/1994 | Wagner et al. |
| 5,388,691 A | * | 2/1995 | White ........................ 206/305 |
| 5,522,899 A | | 6/1996 | Michelson |
| 5,776,199 A | | 7/1998 | Michelson |
| 5,888,223 A | * | 3/1999 | Bray, Jr. .................. 623/17.16 |
| 6,066,175 A | | 5/2000 | Henderson et al. |
| 6,086,613 A | | 7/2000 | Camino et al. |
| 6,235,059 B1 | | 5/2001 | Benezech et al. |
| 6,432,106 B1 | | 8/2002 | Fraser |
| 6,447,544 B1 | * | 9/2002 | Michelson ............... 623/17.16 |
| 6,572,654 B1 | | 6/2003 | Santilli |
| 6,579,321 B1 | | 6/2003 | Gordon et al. |
| 6,613,091 B1 | | 9/2003 | Zdeblick et al. |
| 6,629,998 B1 | * | 10/2003 | Lin .......................... 623/17.11 |
| 6,706,070 B1 | | 3/2004 | Wagner et al. |
| 6,749,636 B2 | | 6/2004 | Michelson |
| 6,793,679 B2 | | 9/2004 | Michelson |
| 6,837,905 B1 | | 1/2005 | Lieberman |
| 6,899,734 B2 | | 5/2005 | Castro et al. |
| 6,962,606 B2 | * | 11/2005 | Michelson ............... 623/17.16 |
| 6,972,019 B2 | * | 12/2005 | Michelson .................... 606/61 |
| 6,984,245 B2 | | 1/2006 | McGahan et al. |

(Continued)

OTHER PUBLICATIONS

Melkent, Anthony J. et al., "Intervertebral Implants with One or More Covers and Methods of Use." Filed on May 1, 2006, 27 pages, U.S. Appl. No. 11/414,888.

(Continued)

*Primary Examiner*—Thomas C Barrett
*Assistant Examiner*—Andrew Yang

(57) ABSTRACT

The present application discloses intervertebral implants and methods of using the implants. The implants may include inferior and superior surfaces, and a sidewall that together form the body of the implant. An inner chamber is formed between the surfaces and the sidewall. An opening extends through the body to access the inner chamber. A cover plate is sized to extend across the opening. The cover plate is adjustable between an open position to access the inner chamber, and a closed position to prevent the bone growth material from escaping from the inner chamber.

8 Claims, 8 Drawing Sheets

U.S. PATENT DOCUMENTS

| | | |
|---|---|---|
| 6,991,653 B2 | 1/2006 | White et al. |
| 7,014,659 B2 | 3/2006 | Boyer, II et al. |
| 2003/0191531 A1 | 10/2003 | Berry et al. |
| 2004/0092929 A1 | 5/2004 | Zindrick |
| 2005/0124993 A1 | 6/2005 | Chappuis |

OTHER PUBLICATIONS

Synthes, "Solution auto-stable pour les fusions intersomatiques par voie antérieure." SynFix-LR. 1 page.

Drawing. "SynFix as Standalone ALIF." Spine. Dec. 1, 2005. 1 page. vol. 30 No. 23.

\* cited by examiner

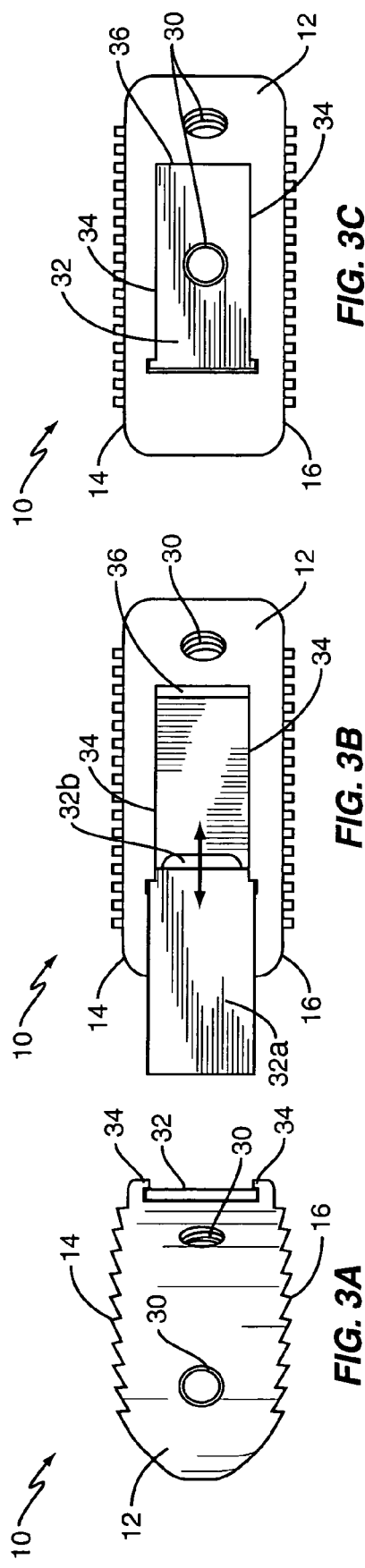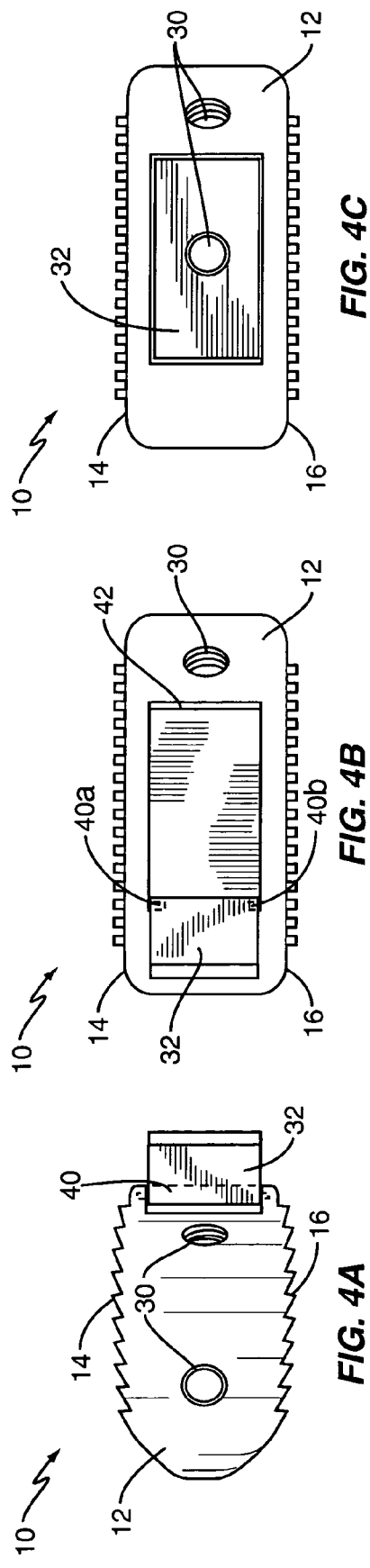

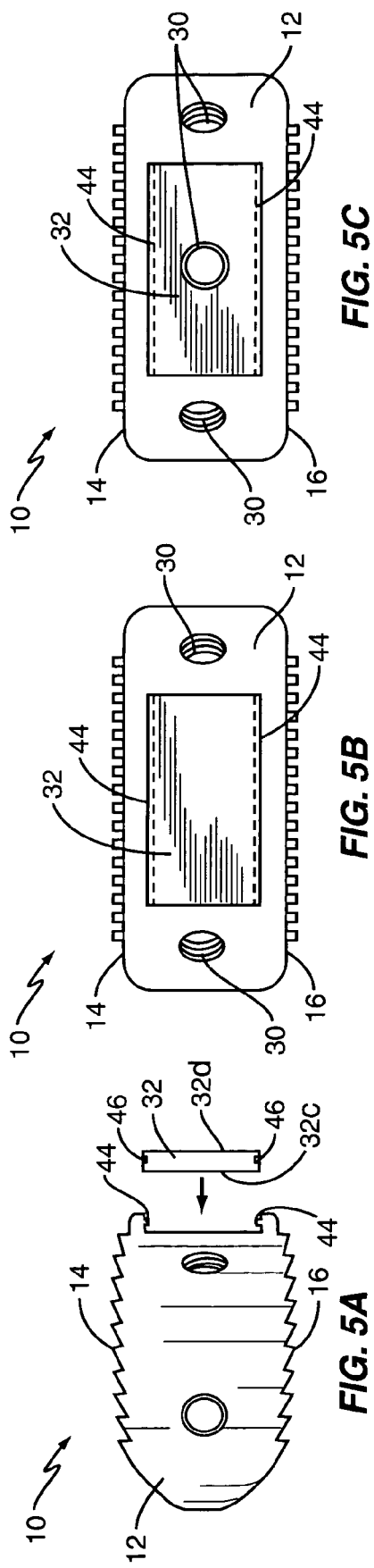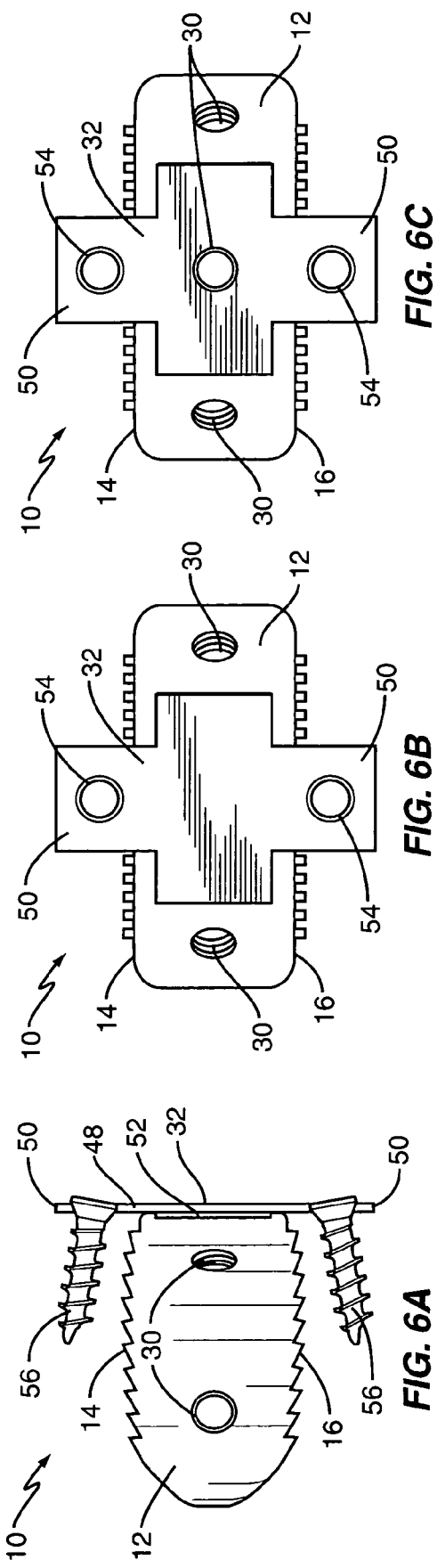

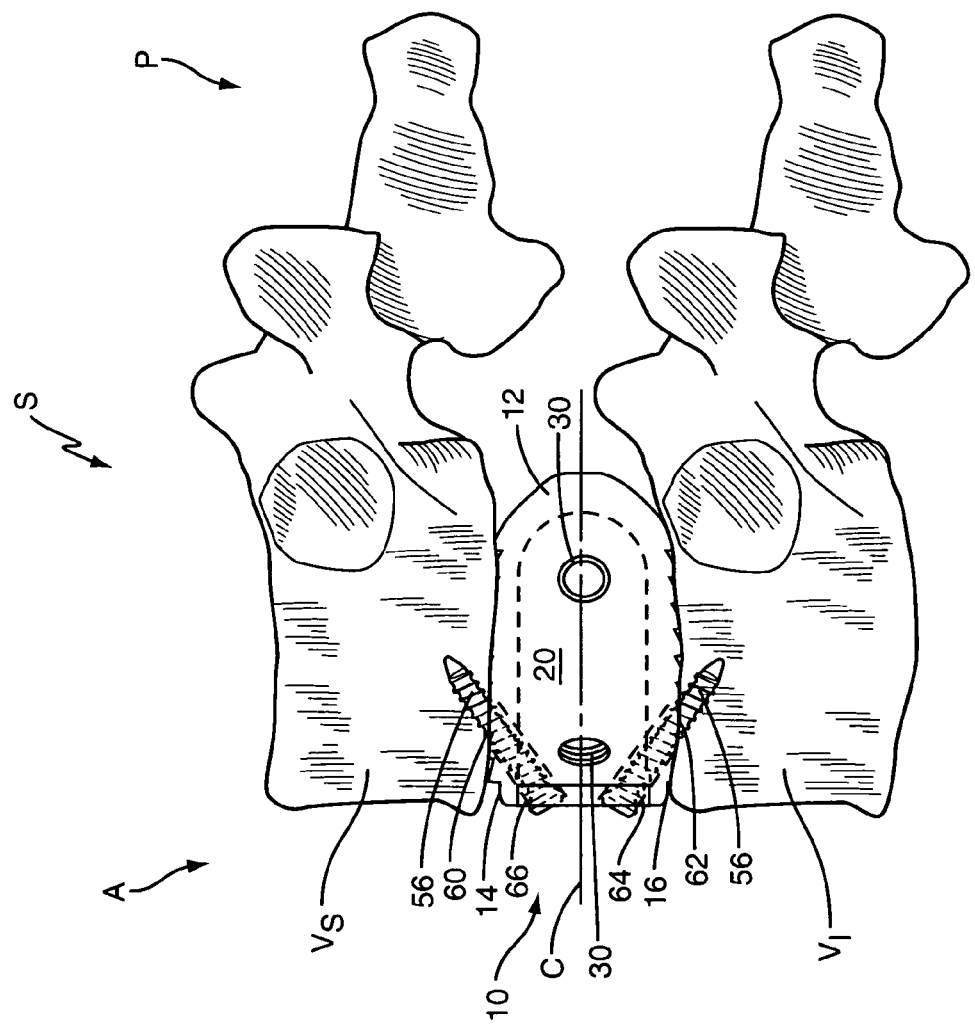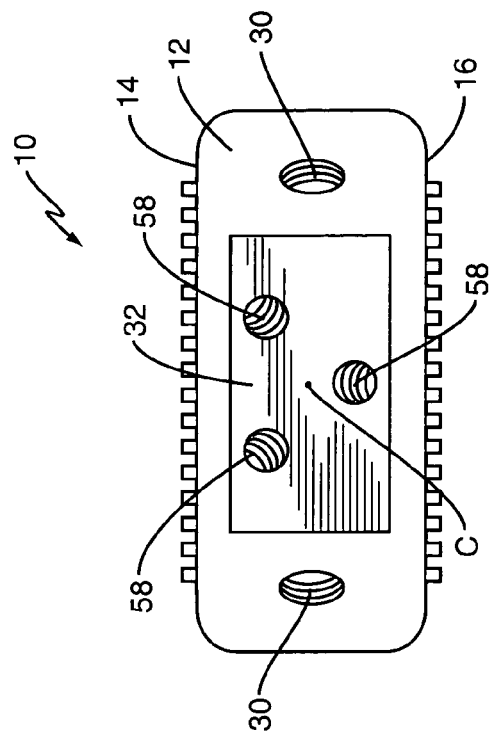
*FIG. 7A*
*FIG. 7B*

INTERVERTEBRAL IMPLANTS WITH COVERED INNER CHAMBER AND METHODS OF USE

BACKGROUND

The present invention relates generally to vertebral implants, and more particularly to intervertebral implants with covers that extend over an interior space.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants may further include bone growth material to facilitate fusion of the implant to one or both adjacent vertebral members. The implant should provide for housing the bone growth material, and prevent inadvertent removal of the material from the implant.

SUMMARY

The present application discloses intervertebral implants and methods of using the implants. The implants may include inferior and superior surfaces, and a sidewall that together form the body of the implant. An inner chamber is formed between the surfaces and the sidewall. An opening extends through the body to access the inner chamber. A cover plate may be sized to extend across the opening. The cover plate may be adjustable between an open position to access the inner chamber, and a closed position to prevent the bone growth material from escaping from the inner chamber.

BRIEF DESCRIPTION OF THE DRAWINGS

FIGS. 3A-3C illustrate perspective views of a cover plate for a vertebral implant according to a first embodiment.

FIGS. 4A-4C illustrate perspective views of a cover plate for a vertebral implant according to a second embodiment.

FIGS. 5A-5C illustrate perspective views of a cover plate for a vertebral implant according to a third embodiment.

FIGS. 6A-6C illustrate perspective views of a cover plate for a vertebral implant according to a fourth embodiment.

FIGS. 7A-7B illustrate perspective views of a cover plate for a vertebral implant according to a fifth embodiment.

DETAILED DESCRIPTION

The present application relates to intervertebral implants. The implants include outer walls that contact the vertebral members. In one embodiment, the implants include a tapered edge to distract the vertebral members during insertion. An inner chamber is formed within the body to hold bone growth material. An opening is formed in one of the exterior walls to access the inner chamber. A cover may be attachable to the implant to close the opening and prevent the bone growth material from escaping from the inner chamber. The implants may include one or more porous surfaces to allow the bone growth material inside of the implant to fuse with the vertebral members.

Figure 1:
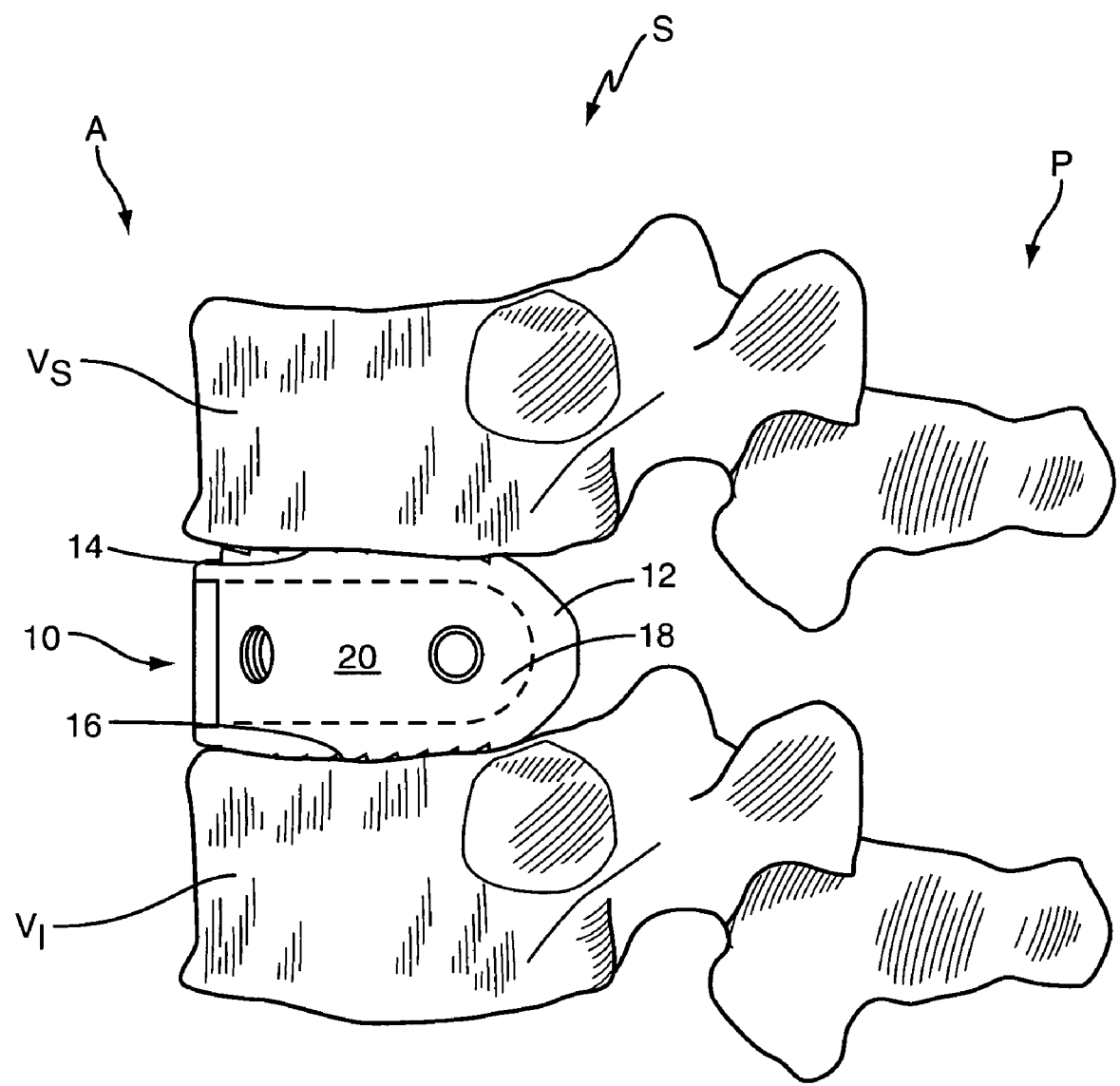
FIG. 1 illustrates a lateral perspective view of one embodiment of a vertebral implant inserted in a patient's spine.

FIG. 1 illustrates a lateral view of one embodiment of an implant 10 positioned within a patient's spine S. For reference, this application indicates the anterior and posterior portions of a patient's body, and the implant 10, using the reference letters 'A' and 'P,' respectively. However, it should be noted that the implant 10 is not limited to any particular configuration or insertion approach with respect to the anterior and posterior portions of the patient.

As seen in FIG. 1, the implant 10 comprises a body 12 sized to fit within the intervertebral space between adjacent vertebral members $V_S$, $V_I$. In this embodiment, the body 12 is shaped to conform to the intervertebral space formed between the vertebral members $V_S$, $V_I$, however, other shapes are also possible. The body 12 includes superior surface 14, an inferior surface 16, and a surrounding sidewall 18 that substantially enclose an inner chamber 20. The superior and inferior surfaces 14, 16 may be substantially flat, or may include a curved shape to conform to the shape of the vertebral members $V_S$, $V_I$. In FIG. 1, the superior surface 14 contacts the lower surface of the superior vertebral member $V_S$, while the inferior surface 16 contacts the upper surface the inferior vertebral member $V_I$. The inner chamber 20 receives bone growth material that, as described below in more detail, grows through the superior and inferior surfaces 14, 16 to fuse with the vertebral members $V_S$, $V_I$.

Figure 2A:
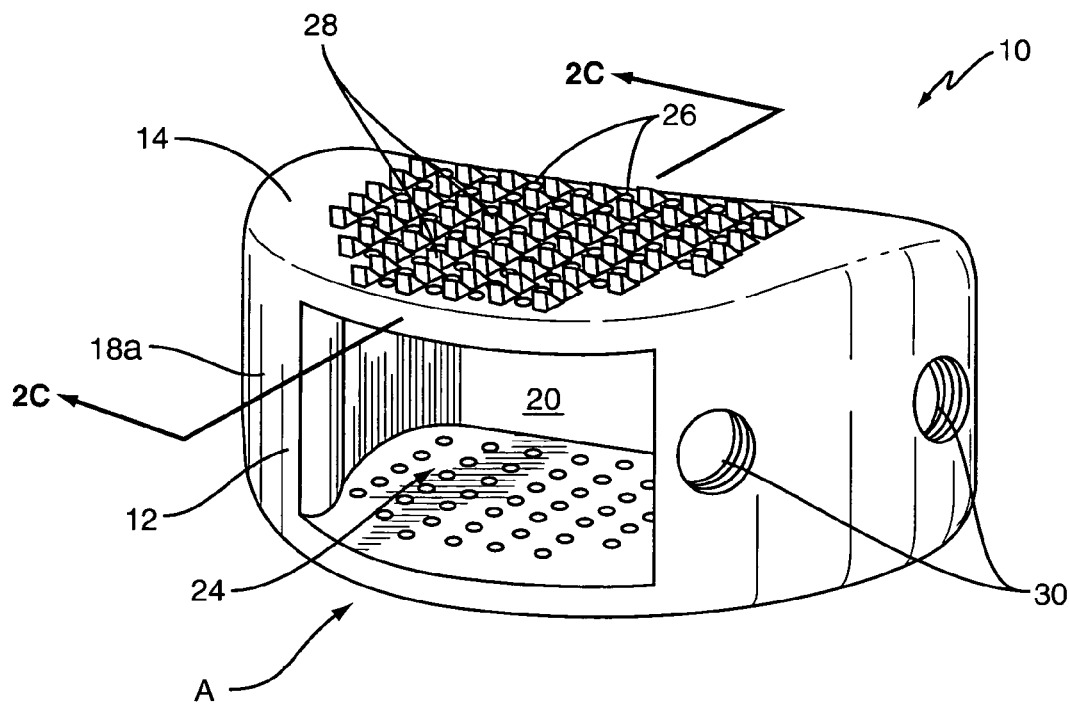
FIGS. 2A-2B illustrate perspective views of a vertebral implant according to one embodiment.
Figure 2B:
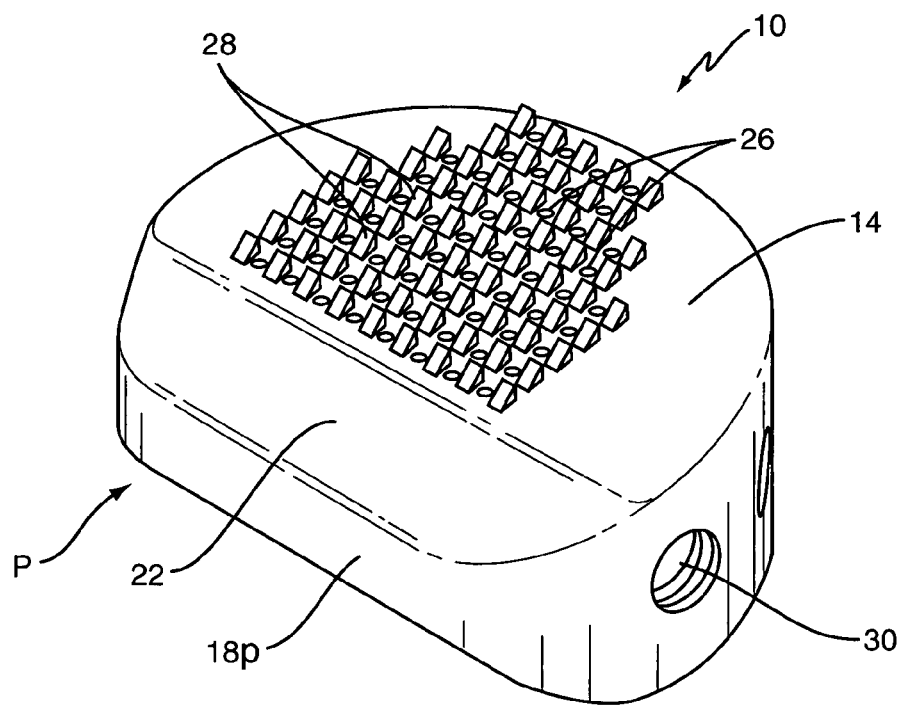

FIGS. 2A-2D illustrate perspective views of an implant 10 formed according to one embodiment. As best seen in FIGS. 2A-2B, the body 12 of implant 10 includes an anterior side A (FIG. 2A), and a posterior side P (FIG. 2B). The sidewall 18a on the anterior side A of body 12 may be arcuate to conform to the shape of the anterior portion of the vertebral members $V_S$, $V_I$. The sidewall 18p on the posterior side P of body 12 is formed to comprise a substantially straight edge. One or both of the superior and inferior surfaces 14, 16 may include a smooth tapered surface 22 that extends downward on the posterior side P to meet the peripheral edges of sidewall 18p. As described later in more detail, the tapered surface 22 reduces the height of the posterior side P of body 12, relative to the anterior side A, to facilitate surgical insertion between the vertebral members $V_S$, $V_I$.

In this embodiment, an opening 24 is formed in the sidewall 18a that opens into the inner chamber 20. The opening 24 provides access to the inner chamber 20 so that a person performing the surgical insertion procedure may pack the inner chamber 20 with bone growth material, which will later fuse with the adjacent vertebral members $V_S$, $V_I$. The inner chamber 20 in this embodiment is formed as a single cavity within an interior of the body 12. In other embodiments, however, the inner chamber 20 comprises a plurality of intercommunicating cavities that may be at least partially separated by one or more inner walls (not shown).

The material used to construct the body 12 may be a non-porous material, such as surgical steel, for example. Therefore, a plurality of openings 26 may be machined into the superior and inferior surfaces 14, 16 to make those surfaces porous. Particularly, the openings 26 open into the inner chamber 20 to allow the bone growth material to grow through those surfaces 14, 16 and fuse with the vertebral members $V_S$, $V_I$. In this embodiment, the openings 26 are distributed across the surfaces 14, 16 and aligned in rows and columns; however, other patterns are also contemplated. For example, the openings 26 may be arranged in a radial pattern, or a staggered pattern, across one or both of the superior and inferior surfaces 14, 16.

Figure 2C:
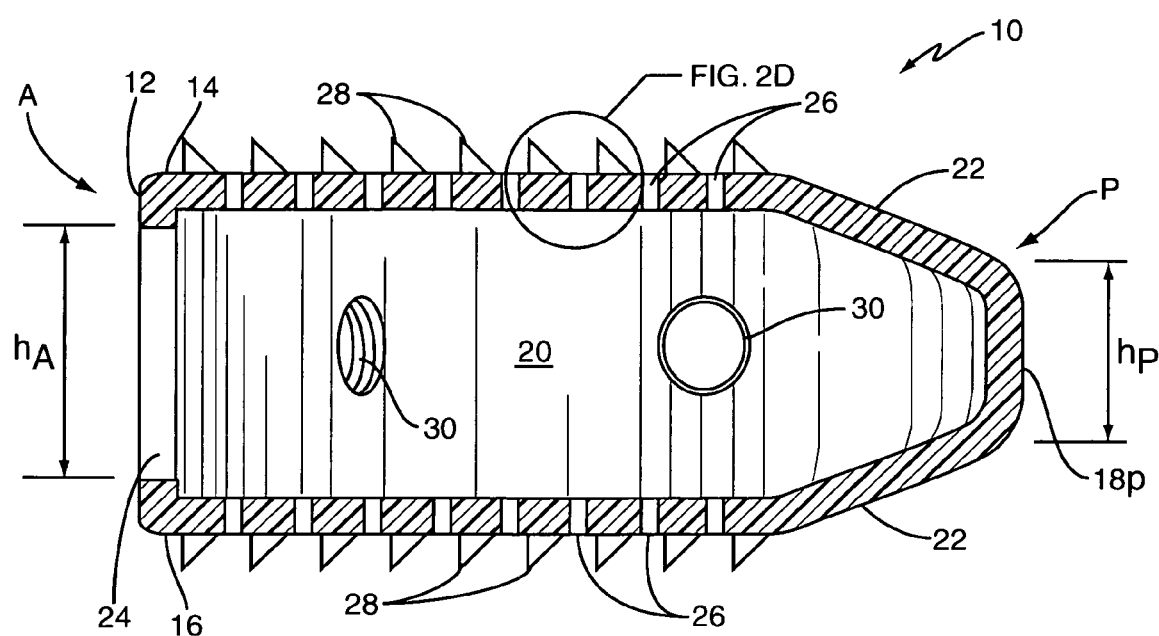
FIG. 2C illustrates a cross-sectional view of one embodiment of a vertebral implant.
Figure 2D:
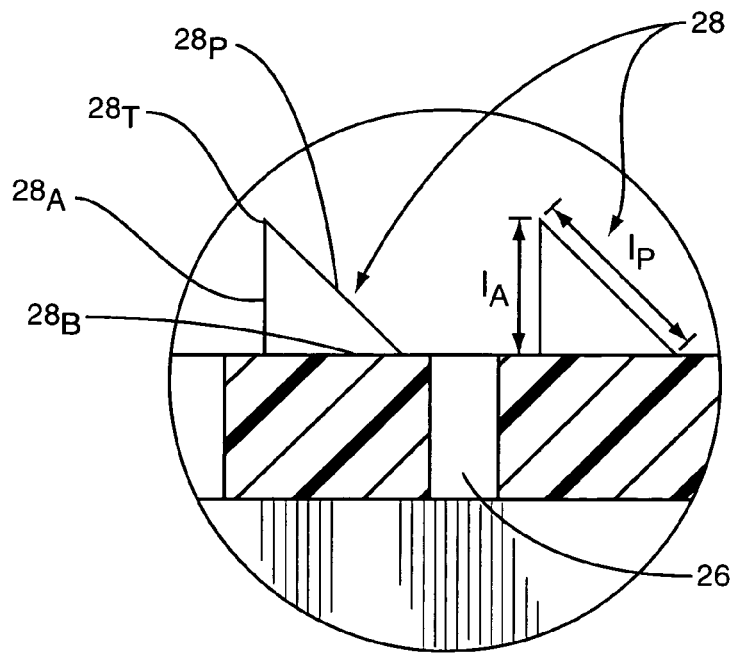
FIG. 2D illustrates a close-up of the teeth disposed on one embodiment of a vertebral implant.
Figure 2E:
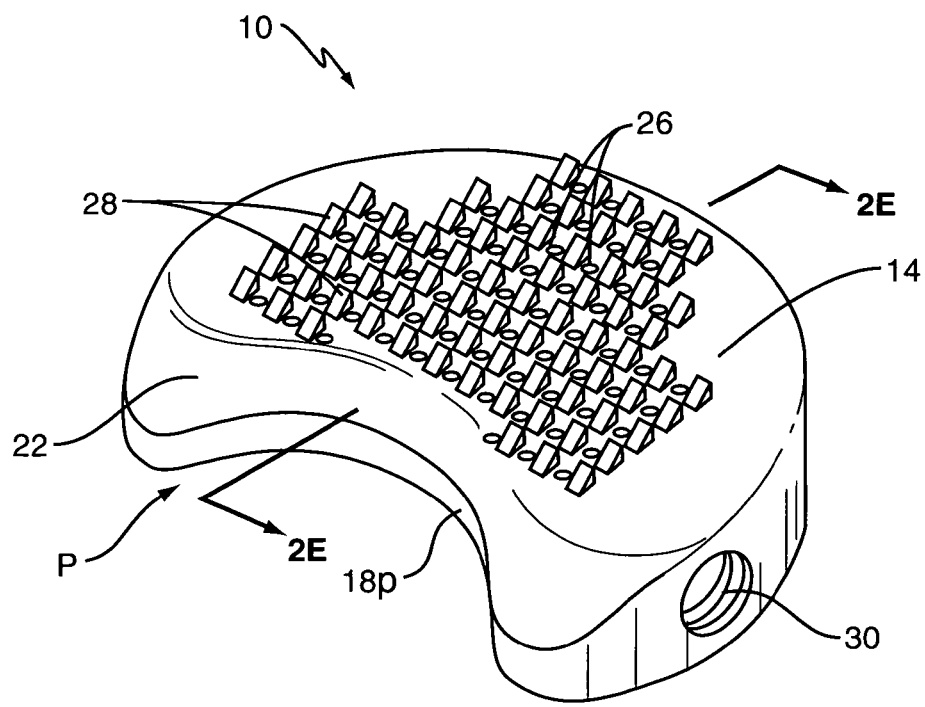
FIG. 2E illustrates a perspective view of a vertebral implant according to one embodiment.
Figure 2F:
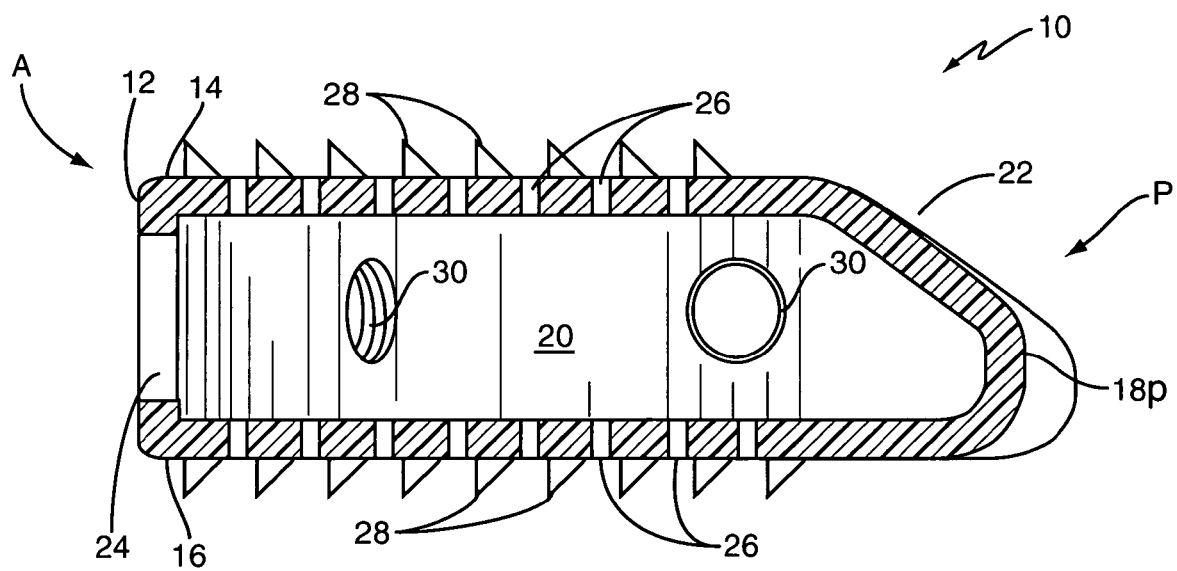
FIG. 2F illustrates a cross-sectional view of a vertebral implant according to one embodiment.
Figure 2G:
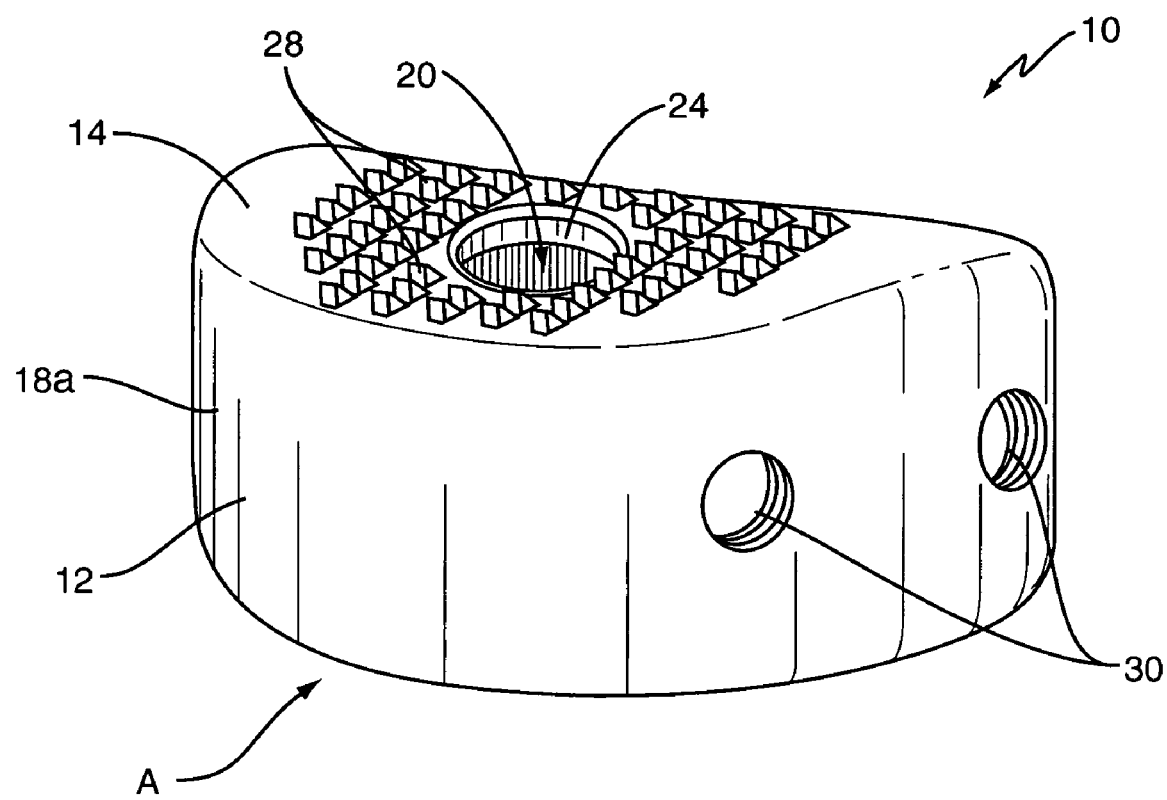
FIG. 2G illustrates a perspective view of a vertebral implant according to one embodiment.

Opening 24 may also be positioned with one or both of the superior and inferior surfaces 14, 16 as illustrated in FIG. 2G. As with the other embodiments, the opening 24 in these surface or surfaces may provide for packing bone growth material within the inner chamber 20, and may facilitate fusion with the vertebral member. Opening 24 may remain open after insertion, or may include a cover (not illustrated in this Figure) that extends over a portion or entirety of the opening 24.

In another embodiment, one or both of the superior and inferior surfaces 14, 16 are constructed of a porous mesh material extending between the sidewall 18. In other embodiments, only portions of one or both of the superior and inferior surfaces 14, 16 are constructed of a porous mesh material, while the remaining portions are non-porous. Whatever the construction of the superior and inferior surfaces 14, 16, however, these surfaces are porous to permit bone growth material packed within the inner chamber 20 to grow outwardly and fuse with the adjacent vertebral members $V_S$, $V_I$.

Teeth 28 may be distributed across one or both of the superior and inferior surfaces 14, 16. FIGS. 2C-2D illustrate the teeth 28 as they might be formed according to one embodiment. In this embodiment, the teeth 28 form a serrated pattern on each surface 14, 16. Each tooth 28 comprises a polygon having a base $28_B$ and an opposing tip $28_T$. The teeth 28 may be solid or hollow, but the surface area of the base $28_B$ is larger than the surface area of the tip $28_T$. Each tooth 28 is further formed such that a length $I_A$ of the anterior side $28_A$ of tooth 28 is shorter than a length $I_P$ of the posterior side $28_P$ of tooth 28. Thus formed, the teeth 28 slant slightly towards the anterior end A of the body 12. This facilitates the insertion of the implant 10 into the intervertebral space using an anterior approach. Once the implant 10 is inserted, the tips $28_T$ of the teeth 28 grip the surfaces of the adjacent vertebral members $V_S$, $V_I$. In this position, the teeth 28 resist removal of the implant 10 in the anterior direction and maintain the alignment of implant 10 within the intervertebral space. In other embodiments, teeth 28 include other shapes and sizes. In one specific example, teeth 28 are substantially symmetrical.

As seen in FIG. 2C, a cross-sectional view of one embodiment of the implant 10 illustrates the body 12 having a substantially bullet-shaped lateral profile. Particularly, the tapered surfaces 22 slope to meet sidewall $18_P$. The tapered surfaces 22 may slope at any desired angle; however in one embodiment, the tapered surfaces 22 slope at substantially the same angle such that a height $h_P$ of the sidewall $18_P$ is less than a height $h_A$ of the opening 24. The reduced height of the body 12 on the posterior side P facilitates insertion of the implant between the vertebral members $V_S$, $V_I$. Particularly, a person performing the surgical insertion procedure may use an insertion tool (not shown) to insert the implant 10 between the vertebral members $V_S$, $V_I$. In one embodiment, the person couples the insertion tool to one or more receptacles 30 formed in the sidewall 18, and inserts the implant 10 into the intervertebral space. The reduced height of the sidewall $18_P$ and the tapered surfaces 22 separate the vertebral members $V_S$, $V_I$ and facilitate entry of the implant 10 into the intervertebral space.

Those skilled in the art will readily appreciate that implant 10 is not limited to the shape illustrated in FIGS. 2A-2C. FIG. 2E illustrates another embodiment where the implant 10 formed with a curved sidewall $18_P$ and including an overall curved or kidney shape. Particularly, the posterior side P of implant 10 may be arcuate such that the posterior sidewall $18_P$ curves inwardly towards the anterior side A of implant 10. The tapered surface 22 and the curved sidewall $18_P$ may permit a person to surgically insert implant 10 without contacting or damaging the patient's spinal cord. The anterior sidewall $18_a$ may be curved or may be substantially straight.

Another embodiment, shown in FIG. 2F, illustrates only the superior surface 14 including the tapered surface 22, while the inferior surface 16 is substantially flat. In other embodiments, only the inferior surface 16 includes a tapered surface 22 and the superior surface 14 extends in a direction substantially perpendicular to the opening 24. Regardless of the embodiment, the tapered surface 22 distracts the adjacent vertebral members $V_S$, $V_I$ to facilitate insertion of the implant 10 into the intervertebral space.

In the figures, the implant 10 is illustrated as being configured to permit surgical insertion using an anterior approach. Therefore, the posterior side P of the body 12 includes a reduced height and the opening 24 is formed on the anterior end A of implant 10. This allows the person inserting implant 10 to pack the inner chamber 20 with the bone growth material from the anterior side of the patient. The person may pack the bone growth material into the inner chamber 20 before, during, or after the insertion procedure. It should be noted, however, that the placement of the opening 24 is not dependent on the surgical approach used to insert the implant 10. As seen in FIGS. 3-7, for example, implant 10 might include a cover plate 32 that may extend over the opening 24. The cover plate 32 prevents the bone growth material within the inner chamber 20 from being expelled during and after the surgical insertion procedure. Thus, the implant 10 may be inserted using any of a variety of surgical approaches including, but not limited to, an anterior approach, a posterior approach, and a lateral approach.

As seen in FIGS. 3-7, the cover plate 32 is movable between an open position and a closed position before and/or after insertion of the implant 10 into the intervertebral space. In the open position, the cover plate 32 allows access to the inner chamber 20 to insert bone growth material. In the closed position, the cover plate 32 extends over the opening 24 to prevent the material from being expelled out of the inner chamber 20. Regardless of the particular embodiment, the cover plate 32 may be constructed of a porous or non-porous material depending on its intended use.

FIGS. 3A-3C illustrate one embodiment of implant 10 including a cover plate 32. In this embodiment, implant 10 comprises a pair of opposing rails 34 extending partially over the opening 24, a cover plate 32 that slidingly engages the rails 34, and a stop 36. The rails 34 are generally rigid and extend laterally across opposing peripheral edges of the opening 24. Rails 34 guide the cover plate 32 as it slides back and forth to cover and uncover the opening 24, and to hold the cover plate 32 in pressing contact with the body 12 over the opening 24. The stop 36 extends along one vertical edge of the opening 24. The stop 36 prevents the cover plate 32 from sliding past the opening 24 when the cover plate 32 slides from the open position (FIG. 3B) to the closed position (FIG. 3C).

The cover plate 32 in this embodiment may include two integrally formed sections. A first section 32a is sized to cover the opening 24, and thus, has dimensions substantially similar to those of opening 24. The second section 32b is slightly offset from the first section 32a such that it extends slightly away from the first section 32a and into the inner chamber 20. The second section 32b is sized to fit behind the stop 36 and contact an inner part of sidewall 18 within inner chamber 20 in the closed position. This resists the cover plate 32 from undesirably moving to the open position after insertion into the intervertebral space. The second section 32b may also contact a vertical edge of the opening 24 on a side opposite the stop 36 when the cover 32 moves to the open position. This prevents the cover 32 from becoming unattached to the body 12 when in the open position. To install the cover plate 32 and move it to the closed position, a user places the cover plate 32 between the rails 34 and the opening 24. The user then slides the cover plate 32 laterally towards the stop 36. To move the cover plate 32 to the open position and access the inner chamber 20, the user slides the cover plate 32 away from stop 36. The cover plate 32 may, as seen in FIG. 3C, include one or more receptacles 30 to receive the insertion tool. The receptacle 30 formed in the cover plate 32 may be in addition to, or in lieu of, those receptacles 30 formed in sidewall 18. In one embodiment, the cover plate 32 may be removed from the body 12. In another embodiment, the cover plate 32 remains attached to the body 12 both in the open and closed positions.

FIGS. 4A-4C illustrate another embodiment where the implant 10 includes one or more hinge mechanisms 40 and a flexible lock 42. In this embodiment, a first hinge mechanism 40a is disposed on a vertical edge of opening 24 proximate the superior surface 14. A second opposing hinge mechanism 40b is disposed on the same vertical edge of opening 24 proximate the inferior surface 16. The cover plate 32 connects to the hinge mechanisms 40 and pivots about the hinge mechanisms 40 between the open (FIG. 4B) and closed (FIG. 4C) positions.

The flexible lock 42 may be disposed on the opposite vertical edge of the opening 24. The flexible lock 42 may, for example, be constructed of a flexible material that tends to bend inwardly towards the inner chamber 20 responsive to the cover plate 32 being closed. The flexible lock 42 will resistingly allow a vertical edge of the cover plate 32 to move past the flexible lock 42 when the cover plate 32 pivots to the closed position. After the cover plate 32 is in the closed position, the flexible lock 42 returns to its normal configuration to contact the exterior surface of the cover plate 32. The flexible lock 42 biases the cover plate 32 inwardly towards the inner chamber 20 with enough force to prevent the cover plate 32 from inadvertently moving to the open position during and/or after the insertion procedure. One or more receptacles 30 may be formed in the cover plate 32 of this embodiment to receive the insertion tool in addition to or in lieu of the receptacles 30 formed in the sidewall 18.

FIGS. 5A-5C illustrate another embodiment of implant 10 including a cover plate 32 that "snaps" into and out of the opening 24. In this embodiment, a pair of opposing flexible rails 44 extend inwardly along opposing edges of opening 24. As seen in FIG. 5A, the flexible rails 44 are positioned such that they are slightly inward from the peripheral edges of the opening 24. The cover plate 32 includes a pair of corresponding opposing tracks 46 formed in opposing edges of the cover plate 32. The tracks 46 are formed along the edges of cover plate 32 between an inner surface 32c that faces the inner chamber 20 when in the closed position and an outer surface 32d that faces away from the inner chamber 20. The cover plate 32 is placed in the closed position by pressing the cover plate 32 onto the flexible rails 44. The flexible rails 44 initially bend toward the inner chamber 20 responsive to this pressure, but return to engage the cover plate 32 by snapping into the corresponding tracks 46. In one embodiment, the rails 44 are rigid but the tracks 46 are flexible such that the tracks 46 flex responsive to the pressure applied to engage the cover plate 32 in the closed position. As seen in FIG. 5C, the cover plate 32 may include one or more receptacles 30 to receive the insertion tool in addition to or in lieu of the receptacles 30 formed in sidewall 18.

In another embodiment, the flexible rails 44 are disposed such that they extend downward from the opposing peripheral edges of the opening 24. In this configuration, the flexible rails 44 initially bend toward the inner chamber 20 responsive to the pressure applied to place the cover plate 32 in the closed position. However, the flexible rails 44 return to their original position to engage and remain on the exterior surface of the cover plate 32.

In another embodiment, the rails 44 are substantially rigid to slidingly engage the tracks 46. As above, the cover plate 32 may or may not remain attached to the body 12 in both the open and closed positions.

FIGS. 6A-6C illustrate another embodiment of an implant 10 where the cover plate 32 is formed as a plug that fits over opening 24. In this embodiment, the cover plate 32 includes a flange 48 that includes a pair of opposing tabs 50 and a plug section 52 that is integrally-formed with the flange 48. The plug section 52 is formed to substantially conform to the shape of the opening 24, and may extend slightly into the inner chamber 20 if desired. The flange 48 covers and extends over the opening 24 when the cover plate 32 is in the closed position. As seen in FIGS. 6A-6C, the opposing tabs 50 extend above and below the superior surface 14 and the inferior surface 16. Each tab 50 includes an aperture 54 that receives a mechanical fastener 56, such as a bone screw for example. The mechanical fasteners 56 extend through the tabs 50 and into the superior and inferior vertebral members $V_S$, $V_I$ to secure the cover plate 32 in the closed position. The mechanical fasteners 56 also function to stabilize the implant 10 between the vertebral members $V_S$, $V_I$ after insertion. The cover plate 32 may include the receptacle 30 to receive the insertion tool in addition to, or in lieu of, the receptacles 30 formed in the sidewall 18.

FIGS. 7A-7B illustrate another embodiment of implant 10 that includes a cover plate 32. In this embodiment, the cover plate 32 includes a plurality of apertures 58. The apertures 58 are positioned into cover plate 32 such that they extend through the cover plate 32 at desired angles relative to a center line C that substantially bisects the body 12. Mechanical fasteners 56 extend through the apertures 58 at these angles and into the inner chamber 20. The mechanical fasteners 56 then exit the inner chamber 20 through apertures 60, 62 formed in the superior and inferior surfaces 14, 16 to connect to the adjacent vertebral members $V_S$, $V_I$. As above, this secures the cover plate 32 to the body 12 of implant 10 and stabilizes the implant 10 within the intervetebral space. In one embodiment, the apertures 58 may be threaded to further engage with the mechanical fasteners 56.

As seen in FIG. 7A, the mechanical fasteners 56 extend through passages 64, 66. One end of each passage 64, 66 terminates at an aperture 58 in the cover plate 32. The opposite end of each passage 64, 66 terminates in the aperture 60 or 62 in the superior and inferior surfaces 14, 16, respectively. Each passage 64, 66 extends through the cover plate 32, the inner chamber 20, and one of the superior and inferior surfaces 14, 16.

Further, each of the apertures 58 in the cover plate 32 extend at angles relative to the center line C. Likewise, each passage 64, 66 extends in an angular direction. FIG. 7A is a lateral view of the implant 10 and, therefore, two passages 64, 66 are shown. However in some embodiments, more than two passages may be used. FIG. 7B, for example, illustrates an embodiment that includes three apertures 58. Each forms one end of a passage that extends through the cover plate 32, the inner chamber 20, and one of the superior and inferior surfaces 14, 16. In one embodiment, each passage extends outward in different directions. Each aperture 58 in FIG. 7B extends at a different angle relative to the center line C.

It should be noted that the figures illustrate the various receptacles 30 as being threaded. However, threaded receptacles 30 are not required. Each receptacle 30 described herein may be threaded or not threaded. Additionally, the body 12 may include both threaded and unthreaded receptacles 30.

Surgical approaches to the spine generally fall within broad categories of approaches. These are anterior, posterior, and lateral approaches, as well as combinations of these approaches such as anterior-lateral, posterior-lateral, and oblique approaches. Within each broad category of approach, there are numerous specific approaches tailored specifically for the cervical, thoracic, lumbar, sacral, and coccygela segment of the spine S to be surgically accessed. The preceding description has described the embodiments in the context of an anterior approach. However, it should be understood that the implant 10 may be inserted between any two vertebral members $V_S$, $V_I$ using any of these broad or specific approaches.

A variety of materials may be positioned within the inner chamber 20 to facilitate fusion of the vertebral members. Suitable examples of bone growth promoting substances include bone morphogenic protein (BMP), LIM mineralization protein (LMP), demineralized bone matrix (DBM), mesenchymal stem cells, blood platelet gel, and biological materials. Other materials are disclosed in U.S. Patent Application Publication Nos. 2005/0203206 and 2006/0025861, each herein incorporated by reference.

The present invention may be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. An intervertebral implant comprising:
    a body including first and second surfaces and a sidewall extending between the first and second surfaces;
    an inner chamber formed within an interior of the body between the first and second surfaces and the sidewall, the inner chamber being sized to receive bone growth material;
    an opening within the body that opens into the inner chamber, the opening including a rail positioned at an edge of the opening; and
    a cover movable between an open position and a closed position, and including a plug integrally formed with the cover that extends into the inner chamber in the closed position and opposing tabs that each includes apertures that are positioned outward beyond the body in the closed position, the cover including a greater thickness at the plug than at the tabs.

2. The implant of claim 1 wherein the opening is positioned in the sidewall of the body.

3. The implant of claim 1 wherein the cover comprises a receptacle sized to receive a tool to insert the implant into a patient.

4. An intervertebral implant comprising:
    a body including first and second surfaces and a sidewall extending between the first and second surfaces;
    an inner chamber formed within an interior of the body between the first and second surfaces and the sidewall, the inner chamber being sized to receive bone growth material;
    an opening within the body that opens into the inner chamber, the opening being the largest passage into the inner chamber; and
    a cover movably attached to the body between an open position to provide access to the inner chamber and a closed position, the cover including a flange with first and second opposing tabs and a plug, the cover including a greater thickness at the plug than at the tabs;
    with the cover in the closed position, the plug extends across the opening of the body to prevent escape of the bone growth material and the first tab extends beyond a superior-most section of the body and the second tab extends beyond an inferior-most section of the body, each of the first and second tabs including apertures that are positioned beyond the body.

5. The implant of claim 4 wherein the opening is positioned in the sidewall of the body.

6. The implant of claim 4 wherein the cover further comprises an aperture sized to receive a fastener to attach the implant to a vertebral member.

7. An intervertebral implant comprising:
    a body including opposing superior and inferior surfaces, and a sidewall extending between the superior and inferior surfaces, the body further comprising a first aperture within one of the superior and inferior surfaces;
    an inner chamber formed within an interior of the body between the superior and inferior surfaces and the sidewall, the inner chamber being sized to receive bone growth material;
    an opening within the sidewall that opens into the inner chamber, the opening being the largest passage into the inner chamber; and
    a cover movable with respect to the body between an open position and a closed position, the cover including a first tab that extends outward beyond the body in a superior direction and a second tab that extends outward beyond the body in an inferior direction when the cover is in the closed position with the first tab and the superior surface contacting against a first vertebral member and the second tab and the inferior surface contacting against a second vertebral member when the body is inserted between the first and second vertebral members, the cover further includes an integrally-formed plug that extends into the inner chamber when the cover is in the closed position, the cover positioned away from the superior and inferior surfaces.

8. The implant of claim 7 wherein the first aperture comprises a threaded aperture.

* * * * *